United States Patent [19]

Nickell et al.

[11] Patent Number: 4,545,813

[45] Date of Patent: Oct. 8, 1985

[54] 3-CHLOROBENZYL-3,6-DICHLORO-2-METHOXYBENZOATE AS A CITRUS RIPENER

[75] Inventors: Louis G. Nickell, Chicago; Leonard J. Stach, Riverside; George F. Luteri, Mount Prospect, all of Ill.

[73] Assignee: Velsicol Chemical Corporation, Chicago, Ill.

[21] Appl. No.: 619,087

[22] Filed: Jun. 11, 1984

[51] Int. Cl.$^4$ .............................................. E05B 59/00
[52] U.S. Cl. ....................................................... 71/107
[58] Field of Search .......................................... 71/107

[56] References Cited

U.S. PATENT DOCUMENTS

| 3,013,054 | 12/1961 | Richter | 71/107 |
| 3,600,407 | 8/1971 | Levin et al. | 71/107 |
| 3,619,169 | 11/1971 | Zick | 71/107 |
| 3,767,377 | 10/1973 | Poulos | 71/107 |

FOREIGN PATENT DOCUMENTS 988074  4/1965  United Kingdom ............... 71/102

Primary Examiner—Paul J. Killos
Attorney, Agent, or Firm—Robert J. Schwarz

[57] ABSTRACT

The subject matter of this invention is the use of 3-chlorobenzyl-3,6-dichloro-2-methoxybenzoate to increase the recoverable sugar in citrus.

7 Claims, No Drawings

3-CHLOROBENZYL-3,6-DICHLORO-2-METHOXYBENZOATE AS A CITRUS RIPENER

This invention relates to the use of 3-Chlorobenzyl-3,6-Dichloro-2-Methyoxybenzoate to increase the recoverable sugar in citrus.

The following demonstrates the preparation of this compound:

EXAMPLE 1

Preparation of 3-Chlorobenzyl-3,6-Dichloro-2-Methoxybenzoate

N-Chlorobenzyl alcohol (14.2 grams; 0.1 mol); toluene (100 ml); triethylamine (10.1 grams; 0.1 mol) and dicamba acid chloride (24.0 grams; 0.1 mol) were placed in a 250 ml glass, round bottom flask equipped with stirrer, thermometer, and heating mantle and heated to 75° C. with stirring for five hours. The mixture was cooled to room temperature overnight and the triethylamine hydrochloride filtered from the solution which was then washed twice with 5% hydrochloric acid and twice with water. After being dried over magnesium sulfate, the toluene was removed and the product recrystallized twice from ethanol. The product has a melting point of 39°–41° C.

Elemental Analysis:

|   | Theoretical (%) | Found (%) |
|---|---|---|
| C | 52.13 | 52.12 |
| H | 3.21 | 3.18 |
| Cl | 30.78 | 30.67 |

It has been unexpectedly found that the recoverable sugar content of citrus can be increased by the applying to the citrus an effective amount of the 3-chlorobenzyl-3,6-dichloro-2-methoxybenzoate.

The term "citrus" includes, but is not limited to, tangerines, oranges, limes, lemons, grapefruit and related plants.

In practicing the invention it is important to realize that the sugar content rends to fluctuate from plant to plant. Therefore, application of the compound will not result the same increase in sugar level in the same amount of time. Generally, the compounds should be applied at from 4 to 40 days prior to the intended harvest time. In some plants it may be possible to increase the sugar level by application as little as 4 days prior to harvest, whereas in the majority of cases, application at from 7 to 28 days prior to harvest is preferable.

The compounds are applied at a rate of from 1 to 50 ounces per acre and 2 to 5 ounces is optimal. Above 5 ounces per acre the increase in effect is nominal, especially in view of the increased cost of the compound applied.

The compounds are employed in the form of aqueous solutions of dispersions. Generally, where the application device is a spray gun, boom or other device where the solution is expressed through a narrow orifice by pressure, the application rate is 50 to 200 gallons of solution per acre. Where the application is by means of an air sprayer (e.g. a "speed sprayer"), i.e. the solution is entrained in a fast moving air stream, more concentrated solutions are employed and about 5 to 50 gallons per acre can be used. Regardless of the amount of solution employed, the pounds of active ingredients per acre should be within the ranges described above.

In the aqueous solutions employed, it is preferred to use a sufactant to prevent the solution from forming globules and "rolling off" upon contact with the leaves of the plant. The surfactant level is generally from 0.1 to 15% by volume of the total formulation and 0.1 to 1 ½% preferred. Suitable surfactants which can be employed include: sorbitan monolaurate; sorbitan monopalmitate; sorbitan monostearate; sorbitan monooleate; sorbitan trioleate; polyoxyethylene sorbitan monolaurate; polyoxyethylene sorbitan monopalmitate; polyoxyethylene sorbitan monostearate; polyoxyethylene sorbitan tristearate; polyoxyethylene sorbitan monooleate; polyoxyethylene sorbitan trioleate; polyoxyethylene cetyl ether; polyoxyethylene stearyl ether and polyoxyethylene oleyl ether.

The above materials are commonly available under trade names such as "Tween", "Span", "Brij" and "Carbowax". Other surfactants which reduce surface tension can also be employed.

In order to demonstrate the usefulness of 3-chlorobenzyl-3,6-dichloro-2-methoxybenzoate in increasing the recoverable sugar in citrus, tests were performed on Satsuma Madarin Oranges. In the tests the results are shown by the Brix readings, coloring and acid content. The Brix value is determined by randomly selecting one or more citrus fruit, squeezing out the juice, filtering if necessary to remove solids, and "reading" the juice with a hand refractometer to determine the % Brix. The test were performed on Satsuma Mandarin Oranges. The results of these experiments are as follows:

EXAMPLE 2

| Concentration (ppm) | Frequency of Spraying | Coloring | Brix | Acids |
|---|---|---|---|---|
| 50 | 1 | 7.3 | 10.0 | 0.71 |
| " | 2 | 7.1 | 10.3 | 0.76 |
| 100 | 1 | 7.0 | 10.1 | 0.73 |
| " | 2 | 8.3 | 10.2 | 0.71 |
| Control |  | 6.2 | 9.2 | 0.78 |

We claim:

1. A method of increasing the recoverable sugar in citrus which comprises applying to the grapes an effective amount of 3-chlorobenzyl-3,6-dichloro-2-methoxybenzoate.

2. The method of claim 1 wherein the amount of 3-chlorobenzyl-3,6-dichloro-2-methoxybenzoate is from about 1 to about 50 ounces per acre.

3. The method of claim 2 wherein the 3-chlorobenzyl-3,6-dichloro-2-methoxybenzoate is applied to the citrus plate at from about 4 to about 40 days prior to harvest.

4. The method of claim 1 wherein the citrus is oranges.

5. The method of claim 1 wherein the citrus is grapefruit.

6. The method of claim 1 wherein the citrus is lemons.

7. The method of claim 1 wherein the citrus is tangerines.

* * * * *

UNITED STATES PATENT OFFICE
CERTIFICATE OF CORRECTION

PATENT NO. : 4,545,813
DATED : October 8, 1985
INVENTOR(S) : Louis G. Nickell, Leonard J. Stach, George F. Luteri It is certified that error appears in the above-identified patent and that said Letters Patent are hereby corrected as shown below:

Claim 1, line 2, change "grapes" to read

-- citrus --

Signed and Sealed this

Third Day of June 1986

[SEAL]

Attest:

DONALD J. QUIGG

Attesting Officer

Commissioner of Patents and Trademarks